United States Patent
Knothe

(12) United States Patent (10) Patent No.: US 6,578,439 B2
(45) Date of Patent: Jun. 17, 2003

(54) SHEET VINYL FLOORING SAMPLING METHOD

(76) Inventor: Dave W. Knothe, 854 Edgewater Dr., Orlando, FL (US) 32804

( * ) Notice: Subject to any disclaimer, the term of this patent is extended or adjusted under 35 U.S.C. 154(b) by 0 days.

(21) Appl. No.: 10/196,869

(22) Filed: Jul. 16, 2002

(65) Prior Publication Data

US 2003/0015044 A1 Jan. 23, 2003

Related U.S. Application Data

(60) Provisional application No. 60/305,779, filed on Jul. 17, 2001.

(51) Int. Cl.[7] .................................................. G01N 1/04
(52) U.S. Cl. ...................................... 73/864.41; 83/919
(58) Field of Search ......................... 73/864.41, 864.51, 73/864.44; 83/919

(56) References Cited

U.S. PATENT DOCUMENTS

| 4,046,046 A | * | 9/1977 | Pearson et al. ................ 83/745 |
| 4,144,760 A | | 3/1979 | Schlueter et al. |
| 4,236,402 A | * | 12/1980 | McGuire ........................ 73/12 |
| 4,805,468 A | | 2/1989 | Choudhry |
| 4,845,896 A | * | 7/1989 | Mercaldi ..................... 51/33 R |
| 4,860,599 A | * | 8/1989 | Griffis ..................... 73/864.45 |
| 4,887,413 A | * | 12/1989 | Tuckey, Jr. .................. 53/520 |
| 4,991,452 A | * | 2/1991 | Dillard et al. ........... 73/864.44 |
| 5,005,433 A | | 4/1991 | Patton |
| 5,046,301 A | * | 9/1991 | Adkins ........................ 53/435 |
| 5,296,083 A | | 3/1994 | Petino |
| 5,373,748 A | | 12/1994 | Lioy et al. |
| 5,395,479 A | | 3/1995 | Petino |
| 5,582,298 A | | 12/1996 | Clayton et al. |
| 5,709,767 A | | 1/1998 | Petino |
| 2002/0121133 A1 | * | 9/2002 | Hudson |

* cited by examiner

*Primary Examiner*—Helen Kwok
*Assistant Examiner*—Charles D Garber
(74) *Attorney, Agent, or Firm*—William M. Hobby, III

(57) ABSTRACT

A sheet vinyl flooring asbestos sampling method includes taking a sample of sheet vinyl flooring without dispensing airborne asbestos fibers. The process includes selecting and cleaning a floor sampling site for attaching a floor sampling template to guide the cutting of the flooring and to limit the liberation of asbestos fibers to the ambient air. A sampling container has an opening thereinto with a flat cutting surface adjacent the opening and a cap to fit over the opening so that the sample may be removed by pushing the cutting edge into the vinyl flooring to cut loose a sample which is pushed into the opening of the container. A cap is then placed over the opening of the container and the sampling container and sample is placed within a storage bag for delivery to a testing lab. The process also includes covering the sampling site with a seal having identification material thereon and also the placing of identification information in the storage bag. A wetting agent is used over the cut area of the floor sampling sight and template and on the cutting blade of the sampling tool.

15 Claims, 1 Drawing Sheet

SHEET VINYL FLOORING SAMPLING METHOD

This Appln claims the benefit of Prov. No. 60/305,779 filed Jul. 17, 2001.

BACKGROUND OF THE INVENTION

The present invention relates to the sampling and testing for asbestos and particularly to the sampling of friable asbestos in sheet vinyl flooring and floor tile. Friable asbestos has sometimes been used in the adhesives for attaching sheet vinyl flooring in floor tile and in the underside of the sheet vinyl flooring in older buildings. The adhesive and underside of the sheet vinyl flooring is isolated from the air in the building by the sheet vinyl covering. However, if the vinyl flooring has to be removed for any reason, such as in a damaged building, which involves an insurance claim or when a building is being razed, it is important to determine whether the sheet vinyl flooring contains any asbestos in the backing since the removal of the flooring will then allow the friable asbestos to contaminate the air. It thus becomes important to test sheet vinyl flooring put in older buildings which have been damaged or which needs to be removed or replaced to determine the cost for insurance claims or before the replacement of sheet vinyl flooring or the razing of a building.

The present invention deals with the sampling of an existing sheet vinyl flooring and tile within older buildings and the testing of the samples for asbestos. The sampling can be performed in accordance with the present method by a lay person without special training (such as an insurance adjuster, contractor, or homeowner) without a certified environment consultant or lab technician having to go to the building to take the samples. Once the sampling has been completed, the sample can be returned to a certified lab where it can be tested for asbestos so that the lab can give a report on the asbestos content.

SUMMARY OF THE INVENTION

A sheet vinyl flooring asbestos sampling method includes taking a sample of sheet vinyl flooring without dispensing airborne asbestos fibers. The process includes selecting and cleaning a floor sampling site for attaching a floor sampling template to guide the cutting of the flooring and to limit the liberation of asbestos fibers to the ambient air. A sampling container has an opening thereinto with a flat cutting surface adjacent the opening and a cap to fit over the opening so that the sample may be removed by pushing the cutting edge into the vinyl flooring to cut loose a sample which is pushed into the opening of the container. A cap is then placed over the opening of the container and the sampling container and sample is placed within a storage bag for delivery to a testing lab. The process also includes covering the sampling site with a seal having identification material thereon and also the placing of identification information in the storage bag. A wetting agent is used over the cut area of the floor sampling sight and template and on the cutting blade of the sampling tool.

BRIEF DESCRIPTION OF THE DRAWINGS

The process of the present invention includes the following items as illustrated in the drawings.

DESCRIPTION OF THE PREFERRED PROCESS

Figure 1:
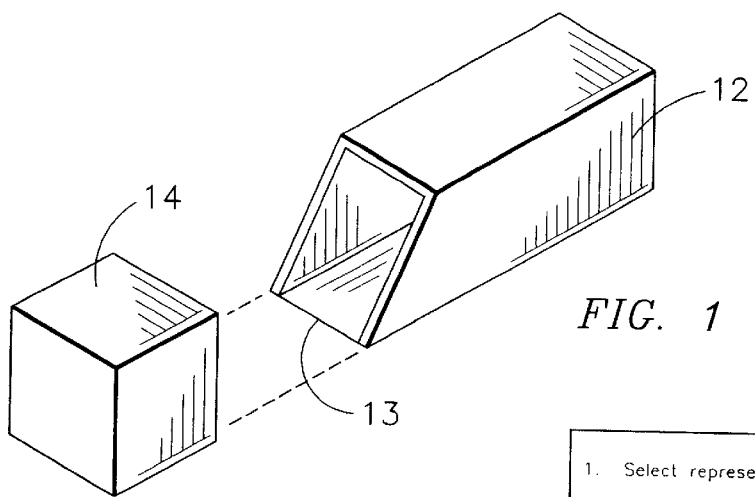
FIG. 1 is an exploded side elevation of a square tubular sampler and the cap therefore.
Figure 2:
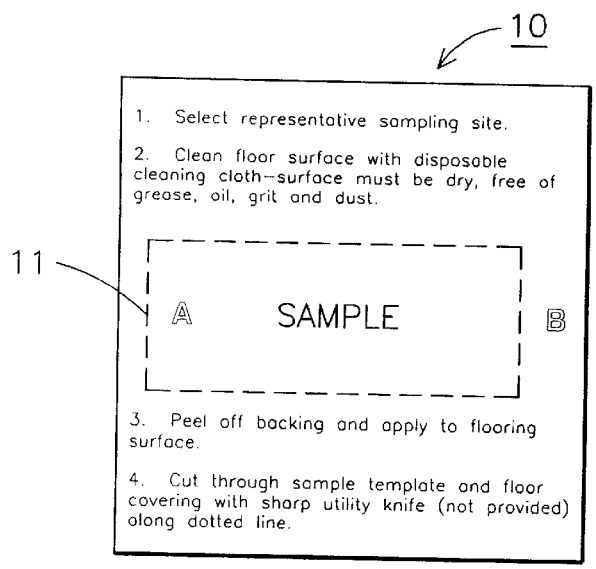
FIG. 2 is a top plan view of a floor sample template.
Figure 3:
FIG. 3 is a perspective view of a wetting solution container.

Sheet vinyl flooring and floor tile products may contain asbestos so that improper sampling can cause liberation of airborne asbestos fibers. Chronic or high level exposure to airborne asbestos can causes respiratory disease so that a requirement of the sampling kit for practicing the present process is the avoidance of improper sampling. The process includes the use of predetermined materials as shown in the drawings in addition to a utility knife for cutting the sheet vinyl flooring for obtaining a sample. The process starts by selecting and identifying the floor covering to be sampled and selecting the representative sampling site. The floor surface of the sampling site is cleaned with a disposable cleaning cloth to be sure that the surface is dry, free of grease, oil grit and dust. This step is followed by the use of a prepared floor sample template, as shown in FIG. 2, which has a covered adhesive backing thereon. The floor sample template 10 has a series of dotted lines 11 to mark the areas for cutting with a utility knife, which cut is made through the floor sample template and through the sheet vinyl flooring therebeneath. The template has the backing peeled off so that it can be applied to the floor surface area before the utility knife is used to cut through the sampling template and floor covering along the dotted lines 11. The wetting agent shown in FIG. 3 is then applied along the cut dotted lines 11 of the template 10 and allowed to set for thirty seconds. The wetting agent can be a common surfactant. The blade of the utility knife is next removed and the utility knife is cleaned on the interior of the knife with a disposable cleaning cloth and the blade is wrapped in the disposable cleaning cloth and placed in a sealable trash bag. The bag is sealed off for later disposal. The wetting agent in FIG. 3 is then applied to the inside of the square tubular sampler 12 cutting end 13, as shown in FIG. 1. The square tubular sampler also has a plastic cap 14 which slides over the open cutting end 13 to seal the sample in the sampling tube 12. Once the wetting solution is applied to the cutting end of the square tubular sampler, the sharp edge of the sampler tube is placed on the template at the cut lines indicated by the letter "A" and the sampler used to cut a sample along the dotted lines 11. The sampler is carefully worked under the sheet vinyl flooring material so that the sample is lifted from the subfloor and moved into the sampler container 12. A general side-to-side motion of the sampler assists in pushing the tube 12 cutting edge 13 through the length of the sample to the point where it has been cut at "B". As the square tubular sample is pushed along the sampling route from A to B, as shown in FIG. 2, the wetting solution is applied to the floor area where the sample has been removed. Constant firm pressure against the subfloor is applied throughout the sampling process and care must be taken to assure that the sample is removed intact.

Figure 4:
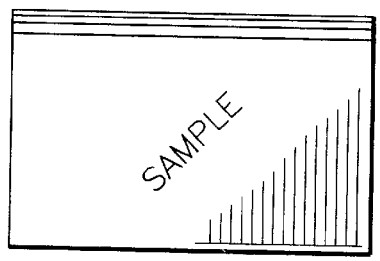
FIG. 4 is a top plan view of a sample storage bag.
Figure 5:
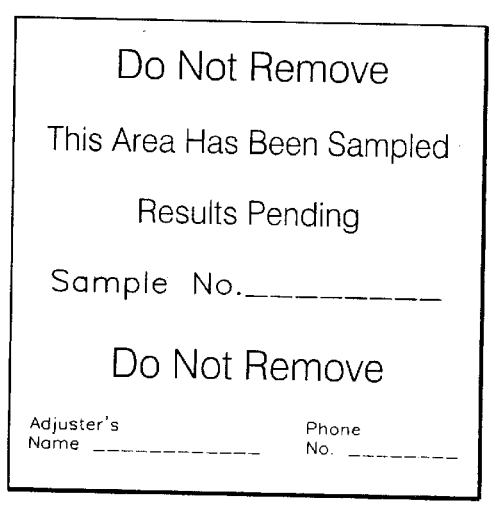
FIG. 5 is a top plan view of a floor sampling site seal.

When the sampler tube 12 of FIG. 1 has been pushed, the entire length of the cut dotted lines from the line at A to the edge indicated by the letter "B", this sample is lifted away from the floor with the intact sample of the sheet vinyl flooring inside the square tubular sampler 12. The plastic end cap 14 of FIG. 1 is now placed over the end of the sampler tube 12 and the sampler is placed into the sample storage bag, shown in FIG. 4. The storage bag is then sealed with the sampler tube 12 having the sheet vinyl flooring sample therein within the bag. Once this has been accomplished, the floor sampling site seal, as shown in FIG. 5, is installed by peeling off the adhesive backing thereon and applying the seal to the clean and dry floor surface, assuring that the seal is adhering to the floor along all four sides. The floor sampling site seal of FIG. 5 has the warning that it should not be removed and that this was the area that had been sampled. It can also have the adjusters or the sample taker's name placed thereon and phone number and the sample numbered for later identification. The sealed sample storage bag of FIG. 4 then has an assessment form containing the information about the location and the samples and sampler's information placed into another large sealable plastic bag and then into a return envelope so that the sample can be returned to the laboratory for testing for asbestos content. The sample is tested using conventional testing techniques.

It should be clear at this time that a process for sampling sheet vinyl flooring in a building for testing for asbestos in the flooring materials has been provided which allows for the sampling in a safe manner for providing samples to a laboratory for testing and disposal of the sample. It will however be clear that the present process should be considered illustrative rather than restrictive.

I claim:

1. A polymer flooring asbestos sampling method comprising the steps of:

selecting and cleaning a floor sampling site on a polymer flooring;

selecting and attaching a floor sampling template to the selected and cleaned floor sampling site;

cutting with a cutting implement through said selected sampling template and polymer flooring;

selecting a sampling container having an opening therein and having a generally flat cutting surface adjacent the opening therein and having a cap for covering the opening therein;

removing a sample of polymer flooring at said selected sampling site with said sampling container flat cutting surface thereby moving a sample of said polymer flooring into said opening therein;

placing said sampling container cap on said sampling container over the opening therein to enclose the sample therein; and placing said sampling container with sample therein within a storage bag for delivery to a testing lab;

whereby a polymer flooring sample can be safely removed for testing for asbestos.

2. The polymer flooring asbestos sampling method in accordance with claim 1 including the step of applying a wetting agent to said cut area of said polymer flooring.

3. The polymer flooring asbestos sampling method in accordance with claim 1 including the step of placing a floor sampling seal over said cut floor sampling site.

4. The polymer flooring asbestos sampling method in accordance with claim 3 including the step of placing a floor sampling seal having warning indicia over said cut floor sampling site.

5. The polymer flooring asbestos sampling method in accordance with claim 4 including the step of placing an adhesive backed floor sampling seal over said cut floor sampling site.

6. The polymer flooring asbestos sampling method in accordance with claim 5 including the step of placing a floor sampling seal having identification information thereon over said cut floor sampling site.

7. The polymer flooring asbestos sampling method in accordance with claim 1 in which the step of selecting and cleaning a floor sampling site is on a sheet vinyl flooring.

8. The polymer flooring asbestos sampling method in accordance with claim 1 including the step of testing said sample in said testing lab.

9. The polymer flooring asbestos sampling method in accordance with claim 1 in which the step of selecting a sampling container includes selecting a container having a generally square tube shape having an opening therein and having a generally flat cutting surface adjacent the opening.

10. The polymer flooring asbestos sampling method in accordance with claim 1 in which the step of selecting and attaching a floor sampling template to the selected and cleaned floor sampling site includes selecting and attaching a floor sampling template having an adhesive backing thereon with a peel off cover.

11. The polymer flooring asbestos sampling method in accordance with claim 5 in which the step of selecting and attaching a floor sampling template includes selecting a template having marking thereon marking cutting area.

12. The polymer flooring asbestos sampling method in accordance with claim 1 in which the step of placing said sampling container with sample therein within a storage bag includes placing sample identification and location information on said storage bag.

13. The polymer flooring asbestos sampling method in accordance with claim 1 including the step of cleaning said cutting implement with a disposable cloth.

14. The polymer flooring asbestos sampling method in accordance with claim 13 including the step of placing said disposable cloth in a sealable cloth.

15. The polymer flooring asbestos sampling method in accordance with claim 1 in which the step of selecting a sampling container having a cap has a plastic cap.

* * * * *